US006225100B1

(12) United States Patent
Maurina-Brunker et al.

(10) Patent No.: US 6,225,100 B1
(45) Date of Patent: May 1, 2001

(54) ARYLSULFOTRANSFERASE

(75) Inventors: Julie Maurina-Brunker, Appleton; Alan D. Grund, Manitowoc, both of WI (US)

(73) Assignee: DCV, Inc., Wilmington, DE (US)

( * ) Notice: Subject to any disclaimer, the term of this patent is extended or adjusted under 35 U.S.C. 154(b) by 0 days.

(21) Appl. No.: 09/214,614

(22) PCT Filed: Jul. 3, 1997

(86) PCT No.: PCT/US97/11794

§ 371 Date: Jan. 8, 1999

§ 102(e) Date: Jan. 8, 1999

(87) PCT Pub. No.: WO98/03636

PCT Pub. Date: Jan. 29, 1998

Related U.S. Application Data

(60) Provisional application No. 60/021,433, filed on Jul. 9, 1996.

(51) Int. Cl.[7] .......................................................... C12N 9/10
(52) U.S. Cl. ............................ 435/193; 435/183; 530/350
(58) Field of Search ..................................... 435/193, 183; 530/350

(56) References Cited

FOREIGN PATENT DOCUMENTS

| 59183690 | 10/1984 | (JP) . |
| 6153936 | 6/1994 | (JP) . |

OTHER PUBLICATIONS

Chai et al., *Bioorganic Chemistry*, 20:181–189 (1992).
Duffel, *Chemico–Biological Interactions*, 92:3–14 (1994).
Khan et al., *Gene*, 137:321–326 (1993).
Kim et al., *Bio Pharm Bull*, 17:1326–1328 (1994).
Kim, et al., *Biol. Pharm. Bull.*, 17:543–545 (1994).
Kim et al., *J. Biochem.*, 102:487–491 (1987).
Kim et al., *Biochimica et Piophysica Acta*, 872:33–41 (1986).
Kim, et al., *J. Biochem.*, 112:456–460 (1992).
Kim et al., *Chem. Pharm. Bull.*, 39:729–731 (1991).
Kim et al., *J. Biochem.*, 109:45–48 (1991).
Kobashi et al., *Arch. Biochem. Biophys.*, 245:537–539 (1986).
Kobashi et al., *Biochem. Biophys. Res. Comm.*, 140:38–42 (1986).
Kobashi et al., *J. Protein Chem.*, 6:237–244 (1987).
Koizumi et al., *Chem. Pharm. Bull.*, 40:1864–1867 (1992).
Koizumi et al., *Chem. Pharm. Bull.*, 39:2638–2643 (1991).
Koizumi et al., *Chem. Pharm. Bull.*, 38:794–796 (1990).
Konishi–Imamura et al., *J. Biochem.*, 115:1097–1100 (1994).
Konishi–Imamura et al., *Biochem. Int'l.*, 28:725–734 (1992).
Konishi–Imamura et al., *J. Enzyme Inhibition*, 8:233–241 (1995).
Konishi–Imamura eta l., *Biol. Pharm. Bull.*, 17:1018–1022 (1994).
Li et al., *Biochem. J.*, 274:355–360 (1991).
Lin et al., *J. Biol. Chem.*, 267:2876–2879 (1992).
Muramatsu et al., *Eur. J. Biochem.*, 223:243–248 (1994).
Niehrs et al., *Chemico–Biological Interactions*, 92:257–271 (1993).
Saidha et al., *Arch. Biochem. Biophys.*, 272:237–244 (1989).
Saidha et al., *Biochem. J.*, 298:45–50 (1994).

*Primary Examiner*—Rebecca E. Prouty
(74) *Attorney, Agent, or Firm*—Sheridan Ross P.C.

(57) ABSTRACT

The present invention relates to novel arylsulfotransferases. In particular, the present invention relates to novel arylsulfotransferas from Clostridium and from *Eubacterium innocuum*.

15 Claims, 5 Drawing Sheets

FIG. 1

"Environmental" fecal samples

Use to inoculate complex media containing appropriate inducers/indicators. Grow under aerobic and anaerobic conditions.

p-nitrophenylsulfate    p-nitrophenol (yellow)    4-methylumbelliferyl sulfate    4-methylumbelliferrone (fluorescent)

Examine cultures for evidence of arylsulfate metabolism

Dilute/plate culture on indicator plates. Pink fluorescent colonies and purify.

Screen strains for arylsulfotransferase activity via HPLC.

Fig. 5

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 11 amino acids
        (B) TYPE: amino acid
        (D) TOPOLOGY: linear      (ii) MOLECULE TYPE: peptide      (xi) SEQUENCE DESCRIPTION: SEQ ID NO:1:

Glu Ala Asp Pro Asn Lys Phe Tyr Gly Leu Met
1               5                 10

(2) INFORMATION FOR SEQ ID NO:2:

(i) SEQUENCE CHARACTERISTICS:
        (A) LENGTH: 2 amino acids
        (B) TYPE: amino acid
        (D) TOPOLOGY: linear      (ii) MOLECULE TYPE: peptide      (xi) SEQUENCE DESCRIPTION: SEQ ID NO:2:

Tyr Arg
1

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear      (ii) MOLECULE TYPE: peptide      (xi) SEQUENCE DESCRIPTION: SEQ ID NO:3:

Tyr Ala Phe Gly Tyr Pro Ser
1               5

(2) INFORMATION FOR SEQ ID NO:4:

```
      (i) SEQUENCE CHARACTERISTICS:
          (A) LENGTH: 5 amino acids
          (B) TYPE: amino acid
          (D) TOPOLOGY: linear (ii) MOLECULE TYPE: peptide (xi) SEQUENCE DESCRIPTION: SEQ ID NO:4:

Arg Tyr Leu Pro Thr
1               5

(2) INFORMATION FOR SEQ ID NO:5:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (xi) SEQUENCE DESCRIPTION: SEQ ID NO:5:

Tyr Gly Gly Phe Leu
1               5

(2) INFORMATION FOR SEQ ID NO:6:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:6:

Asp Tyr Met Gly Trp Met Asp Phe
1               5

(2) INFORMATION FOR SEQ ID NO:7:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (xi) SEQUENCE DESCRIPTION: SEQ ID NO:7:

Asp Arg Val Tyr Ile His Pro Phe His Leu
1               5                   10

(2) INFORMATION FOR SEQ ID NO:8:

(i) SEQUENCE CHARACTERISTICS:
          (A) LENGTH: 10 amino acids
          (B) TYPE: amino acid
          (D) TOPOLOGY: linear (ii) MOLECULE TYPE: peptide (xi) SEQUENCE DESCRIPTION: SEQ ID NO:8:

Glu Gln Asp Tyr Thr Gly Trp Met Asp Phe
1               5                   10

(2) INFORMATION FOR SEQ ID NO:9:

(i) SEQUENCE CHARACTERISTICS:
          (A) LENGTH: 9 amino acids
          (B) TYPE: amino acid
          (D) TOPOLOGY: linear
```

-continued (ii) MOLECULE TYPE: peptide (xi) SEQUENCE DESCRIPTION: SEQ ID NO:9:

Cys Tyr Phe Gln Asn Cys Pro Arg Gly
1               5

(2) INFORMATION FOR SEQ ID NO:10:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:10:

Gly Asp Phe Glu Glu Ile Pro Glu Glu Tyr Leu Gln
1               5                   10

ARYLSULFOTRANSFERASE

This application is a 371 of PCT/0597/11794 which claims the benefit of Provisional Application No. 60/021,433 filed on Jul. 9, 1996.

FIELD OF THE INVENTION

The present invention relates to a novel arylsulfotransferase.

BACKGROUND OF THE INVENTION

Several enzymatic sulfation reactions occur in the human body as post-translational modification of a variety of proteins and peptides. The sulfoconjugation of endogenous and exogenous phenolic compounds is an important detoxification mechanism. Such sulfoconjugation reactions mainly occur in the liver, kidney, lung, erythrocytes, and intestinal epithelial cells. Additionally, a number of peptide hormones, such as cholecystokinin, caerulein and phyllocaerulein, require sulfation of tyrosine residues for full activity. The sulfation of both phenolic compounds and tyrosylpeptides is carried out by arylsulfotransferases (AST). A number of arylsulfotransferases have been described in mammals, fungi, and other eukaryotic organisms. Mammalian arylsulfotransferases transfer the sulfate group from 3'-phosphoadenosine-5'-phosphosulfate to a phenolic acceptor molecule. Recently, it has been shown that arylsulfotransferases from intestinal bacteria are involved in the sulfation and metabolism of some phenolic compounds. The donor substrate specificity of these bacterial arylsulfotransferases is different from that of the mammalian enzymes. The bacterial arylsulfotransferases do not utilize 3'-phosphoadenosine-5'-phosphosulfate as a sulfate donor, but instead can utilize a variety of aryl sulfate donors such as p-nitrophenylsulfate to transfer a sulfate group to both phenolic acceptors and tyrosylpeptides.

Synthetic production of some sulfated proteins is commercially valuable. For example, the tyrosylpeptide cholecystokinin (CCK) is used clinically in association with cholecystography. CCK has also been demonstrated to inhibit food intake in several animal species. CCK and a C-terminal peptide of CCK, CCK-8, are stimulators of exocrine and endocrine pancreatic secretion and gall bladder contraction in humans. To be biologically active, CCK and CCK-8 require sulfation at tyrosine residues.

Current chemical methods for sulfation of tyrosylpeptides are expensive and relatively inefficient. For example, excessive and non-specific side reactions which will occur during the chemical sulfation must be prevented by protecting the amino acid residues of the peptides. Instability of the peptides during the deprotection processes, as well as a general inefficiency of the sulfation process, result in low yields of the final tyrosylpeptide product. Therefore, there is a need for the development of a biocatalytic route for sulfation of peptides and proteins.

SUMMARY OF THE INVENTION

The present invention relates to a novel arylsulfotransferase (AST). More particularly, the present invention relates to a Clostridium arylsulfotransferase, and more particularly to the arylsulfotransferase produced by *Clostridium innocuum* 554 ATCC 55803 (Strain 554WT). In preferred embodiments, an arylsulfotransferase of the present invention catalyzes the transfer of a sulfate group to cholecystokinin-8 with a yield of greater than about 35% and/or maintains greater than about 40% activity for a given substrate for about 2 weeks when stored at 4° C. without being immobilized or otherwise protected.

Another embodiment of the present invention relates to an arylsulfotransferase having a high donor substrate specificity for p-nitrophenylsulfate, estrone sulfate and indoxyl sulfate as substrate donors.

In another embodiment, an arylsulfotransferase of the present invention has all the identifying characteristics of an arylsulfotransferase produced by *Clostridium innocuum* 554 ATCC 55803 (Strain 554WT).

In yet another embodiment, an arylsulfotransferase of the present invention has all the identifying characteristics of an arylsulfotransferase produced by *Eubacterium nodatum* 552 ATCC 55802 (Strain 552WT).

In yet another embodiment, a arylsulfotransferase of the present invention has identifying characteristics selected from a total molecular weight of about 320 kDaltons, 4 subunits having a molecular weight of about 80 kDaltons each, an optimum pH for sulfation activity at about 8.2, a specific activity of greater than about 15.0, maintains greater than about 40% activity for about 2 weeks when stored at 4° C. without being immobilized or otherwise protected, and has an ability to use a wide variety of aryl sulfate donors.

DETAILED DESCRIPTION OF THE INVENTION

One embodiment of the present invention relates to a novel isolated arylsulfotransferase (AST). In a preferred embodiment, the present invention relates to an isolated Clostridium arylsulfotransferase. Another preferred embodiment of the present invention relates to an isolated *Clostridium innocuum* arylsulfotransferase. In another preferred embodiment, an arylsulfotransferase of the present invention has identifying characteristics of the arylsulfotransferase produced by *Clostridium innocuum* 554 ATCC 55803 (Strain 554WT).

A further embodiment of the present invention relates to an isolated arylsulfotransferase from *Eubacterium nodatum*. More particularly, such an arylsulfotransferase has identifying characteristics of an arylsulfotransferase isolated from *Eubacterium nodatum* 552 ATCC 55802 (Strain 552WT). Even more particularly, such an arylsulfotransferase is isolated from *Eubacterium nodatum* 552 ATCC 55802 (Strain 552WT). The present inventors have isolated novel arylsulfotransferases from Clostridium and from *Eubacterium nodatum*. As discussed above, prior to the present invention, arylsulfotransferases had been identified in mammals, fungi, and other eukaryotic organisms. A few arylsulfotransferases have been identified in prokaryotic organisms Eubacterium rectale A-44, Klebsiella K-36 and Haemophilus K-12 (See, for example, Kobashi et al., 1986, *Archives of Biochemistry and Biophysics*, Vol 245, pp. 537–539; Kim et al., 1994, *Biol. Pharm. Bull.*, Vol. 17, pp. 543–545; and Kim et al., 1994, *Biol. Pharm. Bull.*, Vol. 17, pp. 1326–1328). An arylsulfotransferase of the present invention is clearly distinct from previously described bacterial arylsulfotransferases and has several advantages over these other arylsulfotransferases. Arylsulfotransferases that were described prior to the arylsulfotransferase of the present invention have proven to be very unstable during incubation and storage. For example, the arylsulfotransferase of Eubacterium A-44 is reported to lose nearly all of its activity within 48 hours when incubated at 25° C. at pH 8.0 (Kim et al., 1987, *J. Biochem.*, Vol 102, pp. 487–491). The arylsulfotransferase of the present invention, however, is quite stable. For example, as discussed in more detail below, an arylsulfotransferase of the present invention maintains an activity of greater than about 40–50% when stored at 4° C. for several weeks without being immobilized or otherwise protected. Such stability is surprising based on the relative instability of previously described bacterial arylsulfotransferases. Enzyme stability provides significant advantages in terms of commercial utility.

An arylsulfotransferase of the present invention is also superior to the previously described bacterial arylsulfotransferases in a variety of other biochemical characteristics. First, an arylsulfotransferase of the present invention can catalyze the sulfation of acceptor substrates, in particular, CCK-8, with a significantly higher yield than any of the previously described bacterial arylsulfotransferases. Prior to the present invention, the highest reported yield of catalysis of the sulfation of CCK-8 by a bacterial arylsulfotransferase was about a 31.3% yield of sulfated CCK-8 (See Kobashi et al., 1987, *Journal of Protein Chemistry*, Vol. 6, pp. 237–244). In contrast, under similar conditions, a Clostridium arylsulfotransferase of the present invention catalyzes the sulfation of CCK-8 with a yield of up to 60% or greater and a *Eubacterium nodatum* arylsulfotransferase of the present invention catalyzes the sulfation of CCK-8 with a yield of up to 45% or greater. Such yields were quite unexpected, considering the performance of prior bacterial arylsulfotransferases under similar assay conditions. High yields of sulfated CCK-8 using an arylsulfotransferase of the present invention are useful in processes which require the production of biologically active CCK-8.

A second important biochemical characteristic of an arylsulfotransferase of the present invention is that it can have a different donor substrate specificity than previously described arylsulfotransferases. For example, the Eubacterium A-44 arylsulfotransferase of the prior art shows 57% specific activity using p-nitrophenylsulfate as a donor substrate (Kobashi et al., 1987, ibid.). Under similar assay conditions and parameters of measurement (i.e. p-acetylphenylsulfate as a donor baseline at 100% activity), an arylsulfotransferase of the present invention shows about 78% specific activity using p-nitrophenylsulfate as a donor substrate. This significantly higher specific activity of an arylsulfotransferase of the present invention is seen with other donor substrates as well. For instance, again normalizing for p-acetylphenylsulfate as a donor baseline at 100% activity, the specific activity of an arylsulfotransferase of the present invention using estrone sulfate as a donor substrate is about 17%, compared to about 3.4% reported for the Eubacterium A-44 arylsulfotransferase of the prior art (Kobashi et al., 1987, ibid.). With indoxyl sulfate as a donor substrate, an arylsulfotransferase of the present invention has specific activity of about 27%, compared with about 2.2% reported for the Eubacterium A-44 arylsulfotransferase (Kobashi et al., 1987, ibid.). Therefore, an arylsulfotransferase of the present invention has an ability to use a variety of substrate donors with high activity, and is clearly distinguished over the prior art arylsulfotransferases.

As discussed above, current chemical methods for sulfation of tyrosylpeptides are expensive and relatively inefficient. Therefore, there is a need for a biocatalytic method of producing such peptides. The arylsulfotransferase of the present invention has a significant ability to catalyze the sulfation of tyrosylpeptides such as CCK-8 with extremely high yield. In addition, its unique donor substrate specificity and its surprising stability in culture and storage sets forth the novel arylsulfotransferase of the present invention as a superior bacterial arylsulfotransferase.

According to the present invention, an arylsulfotransferase is a protein, and more particularly an enzyme, which catalyzes the transfer of a sulfate group from a donor molecule to an acceptor molecule. Mammalian arylsulfotransferases catalyze the transfer of a sulfate group from 3'-phosphoadenosine-5'-phosphosulfate to a phenolic acceptor substrate. An arylsulfotransferase of the present invention is different from a mammalian arylsulfotransferase in that it does not utilize 3'-phosphoadenosine 5'-phosphosulfate as a sulfate donor. An arylsulfotransferase of the present invention utilizes a wide range of aryl sulfates as sulfate donors. An "aryl" group is an organic group in which one hydrogen atom is removed from an aromatic hydrocarbon. An aryl sulfate is an aryl group with an attached sulfate group. Aryl sulfates that can be utilized as sulfate donors by an arylsulfotransferase of the present invention include, but are not limited to p-nitrophenylsulfate, p-acetylphenylsulfate, 4-methylumbelliferyl sulfate, estrone sulfate, p-nitrocatechol sulfate, phenolphthalein sulfate and indoxyl sulfate.

An arylsulfotransferase of the present invention does not function solely as an arylsulfatase. According to the present invention, an arylsulfatase is an enzyme that catalyzes the hydrolysis of a phenyl sulfate to a phenol and a sulfate, without subsequently transferring the sulfate group to an acceptor molecule.

As used herein, it is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably.

According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis. As used herein, an arylsulfotransferase can be a full-length protein or any homologue of such a protein. Examples of arylsulfotransferase homologues include arylsulfotransferase proteins in which amino acids have been deleted (e.g., a truncated version of the protein, such as a peptide), inserted, inverted, substituted and/or derivatized (e.g., by glycosylation, phosphorylation, acetylation, myristylation, prenylation, palmitoylation, amidation and/or addition of glycerophosphatidyl inositol).

Reference herein to a Clostridium arylsulfotransferase refers to an arylsulfotransferase which is encoded by a nucleic acid molecule derived from a Clostridium microorganism. Similarly, reference herein to a *Eubacterium nodatum* arylsulfotransferase refers to an arylsulfotransferase which is encoded by a nucleic acid molecule derived from a *Eubacterium nodatum* microorganism. Such a nucleic acid molecule can be a nucleic acid molecule from a naturally occurring Clostridium or *Eubacterium nodatum* microorganism which is either an entire (i.e., complete) gene or a portion thereof capable of forming a stable hybrid with the entire gene. More particularly, such a nucleic acid molecule can be at least about 70%, more preferably at least about 80%, more preferably at least about 90% and even more preferably at least about 95% similar to a naturally occurring Clostridium or *Eubacterium nodatum* microorganism arylsulfotransferase nucleic acid molecule. Such a nucleic acid molecule can be produced using recombinant DNA technology (e.g., polymerase chain reaction (PCR) amplification, cloning) or chemical synthesis.

A Clostridium or *Eubacterium nodatum* microorganism refers to any naturally occurring microorganism of the genus Clostridium or the species *Eubacterium nodatum* which is currently known or which is classified as such in the future. More particularly, such a Clostridium microorganism can be a *Clostridium innocuum*. Further, a microorganism can be a mutated microorganism. As used herein, a mutated microorganism is a mutated parental microorganism in which the nucleotide composition of such microorganism has been modified by mutation(s) that occur naturally, that are the result of exposure to a mutagen, or that are the result of genetic engineering. Such mutants of a parental strain of Clostridium or *Eubacterium nodatum* can be isolated by, for example, subjecting a parental strain to at least one round of chemical or physical mutagenesis in order to increase the rate of mutagenesis, thereby increasing the probability of obtaining a microorganism producing increased amounts of arylsulfotransferase, an arylsulfotransferase with improved catalytic abilities, or other improved characteristics. Mutant microorganisms of the present invention can be obtained by genetically-engineering microorganisms to produce increased amounts of an arylsulfotransferase of the present invention. For example, it is within the purview of the present invention to transform a microorganism, and preferably a bacterial microorganism, with nucleic acid molecules encoding enzymes of the arylsulfotransferase biosynthetic pathway obtained from arylsulfotransferase-producing Clostridium or *Eubacterium nodatum* organisms.

A particularly preferred Clostridium microorganism of the present invention is *Clostridium innocuum* 554 ATCC Accession No. 55803. A particulary preferred *Eubacterium nodatum* microorganism of the present invention is *Eubacterium nodatum* 552 ATCC Accession No. 55802. *Clostridium innocuum* 554 ATCC Accession No. 55803 and *Eubacterium nodatum* 552 ATCC Accession No. 55802 were isolated according to the methods of the invention, and were placed on deposit on Jul. 30, 1996, at the American Type Culture Collection (ATCC), located at 12301 Parklawn Drive, Rockville, Md. 20852, under the conditions of the Budapest Treaty on the International Recognition of the Deposit of Microorganisms for the Purposes of Patent Procedure, as exemplars of the organisms disclosed and claimed herein.

Further embodiments of the present invention include the nucleic acid sequence of a nucleic acid molecule encoding an arylsulfotransferase of the present invention and the amino acid sequence of an arylsulfotransferase of the present invention. Based upon the identification of novel arylsulfotransferases as disclosed herein, determining such nucleic acid and amino acid sequences is within the skill of those in the art and within the scope of the invention. For example, nucleic acid sequence encoding arylsulfotransferase proteins of the present invention can be identified using known recombinant DNA techniques (e.g. preparation of degenerate oligonucleotides, PCR amplification, cloning, standard DNA sequencing), such as those described in Sambrook et al., *Molecular Cloning*: A Laboratory Manual, Cold Spring Harbor Labs Press, 1989, which is incorporated herein by reference in its entirety.

Further embodiments of the present invention include recombinant nucleic acid molecules which comprise nucleic acid molecules encoding an arylsulfotransferase of the present invention operatively linked to a transcription control sequence. A further embodiment is a recombinant cell which comprises a recombinant nucleic acid molecule encoding an arylsulfotransferase of the present invention. As used herein, "operatively linked" refers to insertion of a nucleic acid sequence into an expression vector in such a manner that the sequence is capable of being expressed when transformed into a cell. As used herein, an "expression vector" is an RNA or DNA vector capable of transforming a host cell and effecting expression of an appropriate nucleic acid molecule, preferably replicating within the host cell. An expression vector can be either prokaryotic or eukaryotic, and typically is a virus or a plasmid. Construction of desired expression vectors can be performed by methods known to those skilled in the art and expression can be in eukaryotic or prokaryotic systems. Transcription control sequences are sequences which control the initiation, elongation, and termination of transcription.

In one embodiment of the present invention, an arylsulfotransferase of the present invention has a specific activity of greater than about 15.0 as measured in an arylsulfotransferase activity assay. Preferably, an arylsulfotransferase of the present invention has a specific activity of greater than about 30.0, and more preferably, greater than about 50.0, and even more preferably, greater than about 75.0. According to the present invention, specific activity is defined as the number of enzyme units per milligram of protein. 1.0 enzyme unit is the amount of enzyme which causes transformation of 1 mmol of substrate per minute under standard assay conditions. Such an assay to determine arylsulfotransferase activity is performed by combining an aryl sulfate donor with a sulfate acceptor and an arylsulfotransferase of the present invention at an optimum pH (e.g. pH 8.2 using tyramine as a sulfate acceptor) at 37° C. Formation of transformed donor substrate (e.g. p-nitrophenol from p-nitrophenylsulfate) or, alternatively, formation of the sulfated acceptor (e.g. sulfated tyramine), is measured, for example, by the absorbance of such transformed donor substrate or acceptor (wavelength is determined according to the particular donor or acceptor being measured), or by HPLC. In a typical arylsulfotransferase activity assay of the present invention, an aryl sulfate donor substrate is used at about 5.0 mM, a phenolic acceptor is used at about 2.5 mM, and a tyrosylpeptide acceptor is used at about 250–500 mM. It is within the scope of the present invention, however, that one of skill in the art can modify such conditions and concentrations to optimize an assay for a given donor/acceptor combination.

In another embodiment, an arylsulfotransferase of the present invention catalyzes the transfer of a sulfate group to cholecystokinin-8 (CCK-8) with a yield of greater than about 35%, and more preferably greater than about 45%, and even more preferably greater than about 55%, within about 6 hours under conditions as described above for an assay to determine arylsulfotransferase activity. A sulfate group can be donated by any aryl sulfate donor substrate as described above, and preferably is donated by p-nitrophenylsulfate. As discussed previously herein, cholecystokinin-8 is a tyrosylpeptide which stimulates exocrine and endocrine pancreatic secretion and gall bladder contraction in humans. To be biologically active, CCK-8 requires sulfation at tyrosine residues.

An arylsulfotransferase of the present invention sulfates a variety of sulfate acceptors. Preferably, an arylsulfotransferase of the present invention sulfates phenolic compounds and tyrosylsulfates. Phenolic compounds that can be sulfated by an arylsulfotransferase of the present invention include, but are not limited to tyrosine, tyrosine methyl ester, tyramine, phenol, catechol, catechin, methyl p-hydroxybenzoate, 4-methylumbelliferone and methyl paraben. Such acceptors are sulfated with a specific activity as illustrated in Table 5 as described in the Examples section. The activities are determined using p-nitrophenylsulfate as the sulfate donor. The activity associated with a phenolic compound sulfate acceptor is determined as described above for determination of arylsulfotransferase activity.

Tyrosylpeptides that can be sulfated by an arylsulfotransferase of the present invention include, but are not limited to cholecystokinin-8 (SEQ ID NQ:6), kyotorphin (SEQ ID NO:2), dermorphin (SEQ ID NO:3), physalaemin (SEQ ID NO:1), proctolin (SEQ ID NO:4), angiotensin I (SEQ ID NO:7), caerulein (SEQ ID NO:8), arg8 vasopressin (SEQ ID NO:9), hirudin (residues 54–65) (SEQ ID NO:10) and leu enkephalin (SEQ ID NO.5). Such tyrosylpeptides are sulfated with a yield as illustrated in Table 5 (See Examples section). A "yield" refers to the percent of tyrosylpeptide that is sulfated over a period of time. Such a yield is determined by measuring the absorbance of the peptide at 280 nm, for example, or by HPLC, under conditions described above for determining arylsulfotransferase activity.

An arylsulfotransferase of the present invention has the particular advantage over previously described arylsulfotransferases of being stable in the absence of immobilizers or other factors. As used herein, an arylsulfotransferase of the present invention maintains an activity of greater than about 40%, more preferably of greater than about 60%, and even more preferably of greater than about 80%, for about 2 weeks when stored at 4° C., without being immobilized or otherwise protected. In preferred embodiments, an arylsulfotransferase of the present invention maintains such activity for about 4 weeks, and more preferably for about 6 weeks, and even more preferably for about 8 weeks.

In a preferred embodiment, an arylsulfotransferase of the present invention has a high donor substrate specificity for p-nitrophenylsulfate, estrone sulfate and/or indoxyl sulfate. More particularly, using tyramine as a sulfate acceptor and calculating percent donor substrate activity based on p-acetylphenylsulfate as a sulfate donor at 100% baseline activity, an arylsulfotransferase of the present invention has a specific activity of greater than about 60% using p-nitrophenylsulfate as a sulfate donor, and more preferably of greater than about 70%, and even more preferably, of greater than about 75%. An arylsulfotransferase of the present invention has a specific activity (under conditions described above) using estrone sulfate as a sulfate donor of greater than about 5%, and more preferably of greater than about 10%, and even more preferably, of greater than about 15%. An arylsulfotransferase of the present invention has a specific activity (under conditions described above) for indoxyl sulfate as a sulfate donor of greater than about 3%, and more preferably of greater than about 15%, and even more preferably, of greater than about 25%.

In accordance with the present invention, microorganisms capable of producing arylsulfotransferases of the present invention are cultured in an effective medium, herein defined as any medium capable of promoting arylsulfotransferase production. Preferably, the effective medium also promotes rapid bacterial growth. Such microorganisms can be cultured in conventional fermentation modes, which include, but are not limited to, batch, fed-batch, and continuous. In a preferred embodiment, an effective medium to be used in accordance with the present invention includes brain heart infusion broth and/or fluid thioglycollate media supplemented with cysteine (0.05%). Preferably, such microorganisms of the present invention are cultured at 37° C. in an anaerobic atmosphere (e.g. 95% nitrogen/5% $CO_2$).

One embodiment of the present invention relates to the isolation of microorganisms capable of producing arylsulfotransferases of the present invention. Such microorganisms are isolated by culturing fecal or sewage samples in medium as described above with the addition of 0.1 mM 4-methylumbelliferyl sulfate and 1 mM p-nitrophenylsulfate as indicators of arylsulfatase activity. Such cultures are then observed daily for aryl sulfate metabolism by examination for fluorescence (indicating formation of 4-methylumbelliferone) and for development of a yellow color (indicating formation of p-nitrophenol). Positive cultures are diluted and plated on a solid form of the above-described indicator media and incubated under anaerobic conditions as described above. Fluorescent and/or yellow colonies which appear are purified and assayed for arylsulfotransferase activity as described above.

An arylsulfotransferase of the present invention can be isolated from a microorganism by any standard method known in the art. In particular, an arylsulfotransferase of the present invention is isolated as described in Example 2 of the Examples section.

It should be appreciated that arylsulfotransferases of the present invention can be produced by any suitable production organism, including microorganisms to which an arylsulfotransferase being produced is either endogenous or heterologous. In a preferred embodiment, the microorganism is Clostridium, and preferably is *Clostridium innocuum*. In another preferred embodiment, the microorganism is *Eubacterium nodatum*. Production of arylsulfotransferases of the present invention by microorganisms to which an arylsulfotransferase is heterologous can be accomplished using microorganisms which have been transformed with a nucleic acid molecule, as defined above, which is operatively linked to an expression vector containing one or more transcription control sequences.

One embodiment of the present invention is an isolated arylsulfotransferase having identifying characteristics of novel arylsulfotransferases identified herein. One such identifying characteristic of an arylsulfotransferase of the present invention is that it has a molecular weight of about 320 kDaltons, and is composed of 4 subunits, each having a molecular weight of about 80 kDaltons. Further such characteristics of an arylsulfotransferase of the present invention preferably include that it has an optimum pH for sulfation activity of about 8.2, a specific activity of greater than about 15.0, maintains an activity of greater than 40% for about 2 weeks when stored at 4° C. without being immobilized or otherwise protected, and has the ability to utilize as sulfate donors an aryl sulfate selected from the group of p-nitrophenylsulfate, p-acetylphenylsulfate, 4-methylumbelliferyl sulfate, estrone sulfate, p-nitrocatechol sulfate, phenolphthalein sulfate and indoxyl sulfate. An additional characteristic is that an arylsulfotransferase of the present invention does not require cofactors for activity.

The following examples are provided for the purposes of illustration and are not intended to limit the scope of the present invention.

EXAMPLES

Example 1

The following example demonstrates the isolation of a Clostridium arylsulfotransferase of the present invention.

Figure 1:
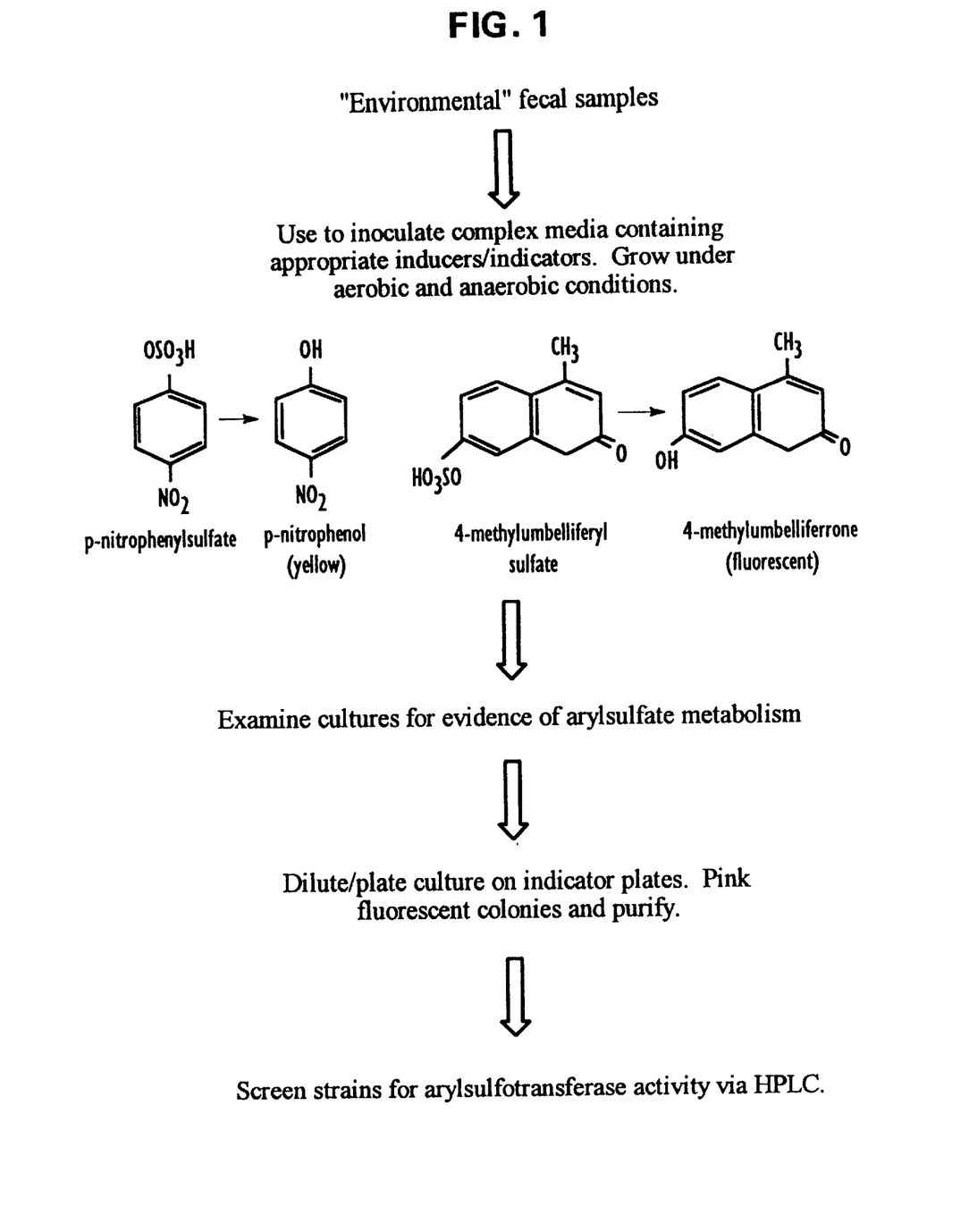
FIG. 1 is a flow chart illustrating the growth and selection process for a Clostridium bacterium which produces an arylsulfotransferase of the present invention.

A number of fecal and sewage samples were screened to identify microbes with arylsulfatase activity. This process is illustrated in FIG. 1. Brain heart infusion broth or fluid thioglycollate media (Difco) supplemented with 0.05% cysteine, and containing 0.1 mM 4-methylumbelliferyl sulfate and 1 mM p-nitrophenylsulfate as indicators were inoculated with fecal or sewage samples. The cultures were grown at 37° C. under aerobic and anaerobic conditions (95% nitrogen/5% $CO_2$). The cultures were examined daily for evidence of aryl sulfate metabolism by inspecting the cultures for formation of methylumbelliferone by long wave UV and for formation of p-nitrophenol by development of a yellow color.

The cultures which tested positive were then diluted and plated on indicator plates containing the same media as above, in solid form. Fluorescent or yellow colonies were selected and purified. The strains were then further examined for AST activity by HPLC.

Obligately anaerobic bacteria were identified as Clostridium which possess an AST that is different from that present in eukaryotes and different from previously isolated AST from other bacterial strains (Table 1). In addition, one obligately anaerobic bacterium, *Eubacterium nodatum*, was also identified as possessing an AST that is different from previously identified strains. These isolates were characterized and identified using biochemical markers and membrane fatty acid analysis. The characterization of the five bacterial arylsulfotransferase-producing isolates (Strains 552WT, 553WT, 554WT, 555WT, and 556WT) is shown in Table 1.

TABLE 1

| Isolate Characteristics | Strain identification | | | | |
|---|---|---|---|---|---|
| | *Eubacterium nodatum* 552WT | *Clostridium innocuum* 553WT | *Clostridium innocuum* 554WT | *Clostridium innocuum* 555WT | *Clostridium inoccuum* 556WT |
| Spores | − | + | + | + | + |
| Gram Stain | + | + | + | + | + |
| Morphology | f | r | r | r | r |
| Esculin | − | + | + | + | + |
| Nitrate Reduction | − | − | − | − | − |
| Indole | − | − | − | − | − |
| Dextrose | − | + | + | + | + |
| Arabinose | − | − | − | − | − |
| Glycerol | − | − | − | − | − |
| Lactose | − | − | − | − | − |
| Maltose | − | − | − | − | − |
| Mannitol | − | + | + | + | + |
| Rhamnose | − | − | − | − | − |

TABLE 1-continued

| Isolate Characteristics | Strain identification | | | | |
|---|---|---|---|---|---|
| | *Eubacterium nodatum* 552WT | *Clostridium innocuum* 553WT | *Clostridium innocuum* 554WT | *Clostridium innocuum* 555WT | *Clostridium inoccuum* 556WT |
| Salicin | − | + | + | + | − |
| Sucrose | − | + | − | + | + |
| Trehalose | − | + | + | + | − |
| Xylose | − | − | − | − | − |
| Cellobiose | − | + | + | + | + |
| Mannose | − | + | + | + | + |
| Raffinose | − | − | − | − | − |
| Sorbitol | − | − | − | − | − |
| Catalase | − | − | − | − | − |
| Urease | − | − | − | − | − |
| Obligate Anaerobe | + | + | + | + | + | r = rods, nonmotile; strains 553–556 form refractile endospores
f = filamentous

Example 2

The following example shows the characterization of arylsulfotransferase from *Clostridium innocuum* 554 ATCC strain 55803 (Strain 554WT).

The AST from a *Clostridium innocuum* isolate (Table 1, Strain 554WT) was purified and studied in more detail. This strain is deposited with ATCC and is referred to herein as *Clostridium innocuum* 554 ATCC 55803(Strain 554WT).

Table 2 illustrates the purification process of the *Clostridium innocuum* 554 ATCC 55803 (Strain 554WT) AST, indicating the specific activity at each stage of purification. At 118 fold purification from crude extract, the specific activity of the AST was 79.0. Therefore, the specific activity of an AST of the present invention is very high.

TABLE 2

| Purification Step | Total Protein | Total Activity | Yield (%) | Specific Activity | Fold Purification |
|---|---|---|---|---|---|
| Crude extract | 276 | 185 | 100 | 0.67 | 1.0 |
| 25–60% ammonium sulfate cut | 188 | 154 | 84 | 0.83 | 1.24 |
| DEAE-cellulose column | 6.95 | 105 | 57 | 15.1 | 22.5 |
| Phenyl hydrophobic interaction column | 1.73 | 62.9 | 34.0 | 36.3 | 54.2 |
| Superdex 200 size exclusion column | 0.17 | 13.1 | 7.1 | 79.0 | 118 |

Figure 2:
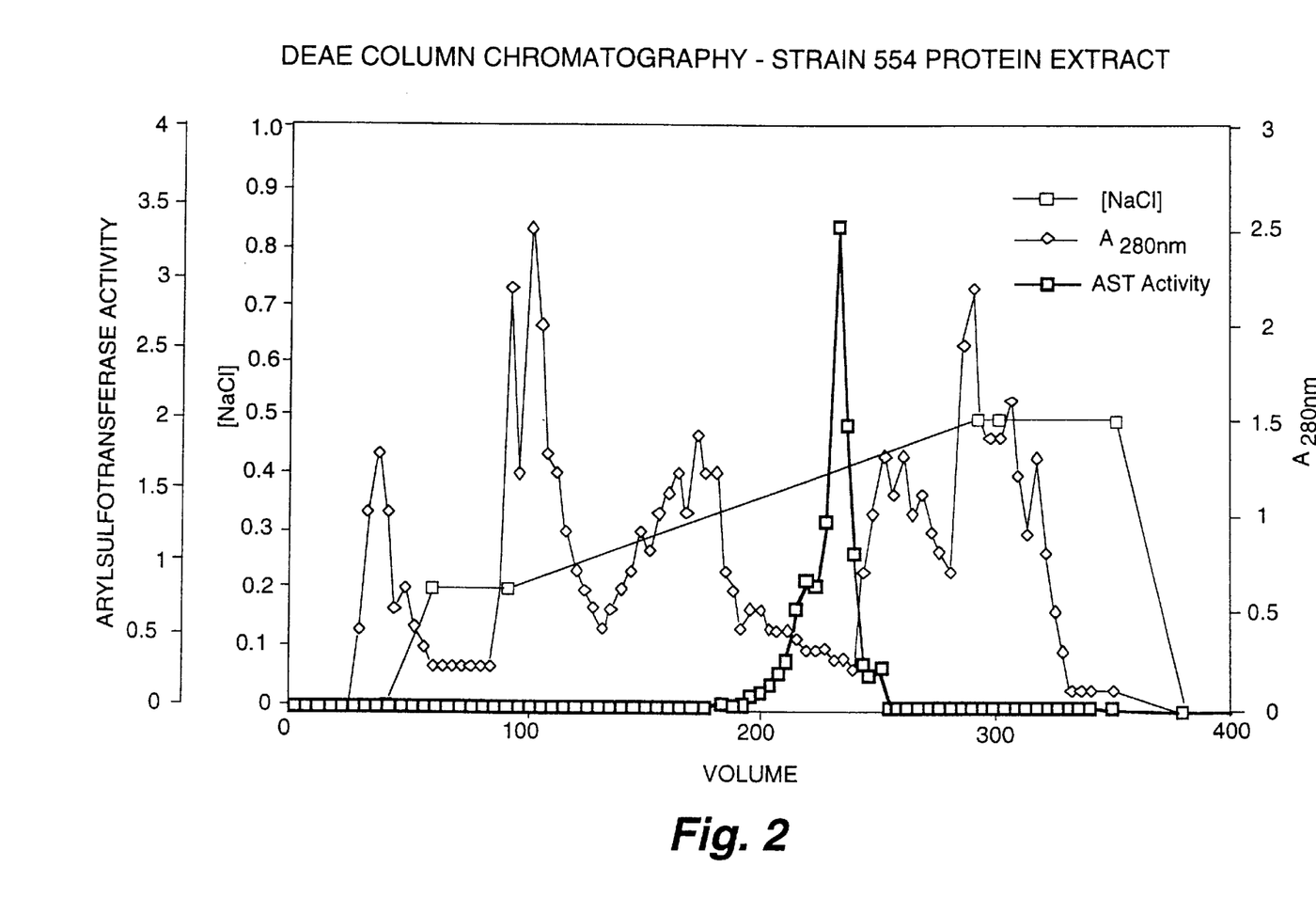
FIG. 2 illustrates the elution and activity profile of an arylsulfotransferase from *Clostridium innocuum* 554 ATCC 55803.

Cells from strain 554WT were grown under anaerobic conditions as described in Example 1 in 10 liter anaerobic cultures. The cells were harvested and stored at 80° C. The cells were then thawed and suspended in breakage buffer (0.1 M Tris, pH 8.0; 5 mM dithiothreitol; 1 mm phenylmethylsulfonyl fluoride, 1 mM bestatin, 1 mM pepstatin and 1 mM leupeptin) plus approximately one third volume of 25 micron glass beads. The cells were then disrupted by sonication with the glass beads for a total of 5–10 minutes. The suspensions were centrifuged at 15,000×g for 20 minutes, and the supernatant containing the crude AST was retained. This material was then fractionated by addition of solid ammonium sulfate to 25% saturation. Following centrifugation, the pellet was discarded and additional ammonium sulfate was added to 60% saturation. After centrifugation, the pellet was retained and resuspended in breakage buffer. This material was then dialyzed overnight against breakage buffer at 4° C. The dialyzed protein solution was then applied to a 2.1×15 cm DEAE cellulose FPLC column (Tosohaus). The AST activity was eluted with a 0–0.5 M NaCl gradient as shown in FIG. 2. AST activity was assayed as described in detail below, and active fractions were pooled, concentrated by ultrafiltration, and applied to a 1.5×15 cm phenyl-5DPW hydrophobic interaction column (Tosohaus). The AST was eluted with a reverse ammonium sulfate gradient. Fractions containing AST, as determined by assay, were pooled, concentrated, and applied to a 2×65 cm Superdex-200 gel exclusion column (Pharmacia). Using molecular weight standards, the native enzyme molecular weight was determined to be 320 kDaltons. Active fractions were pooled and concentrated.

Figure 3:
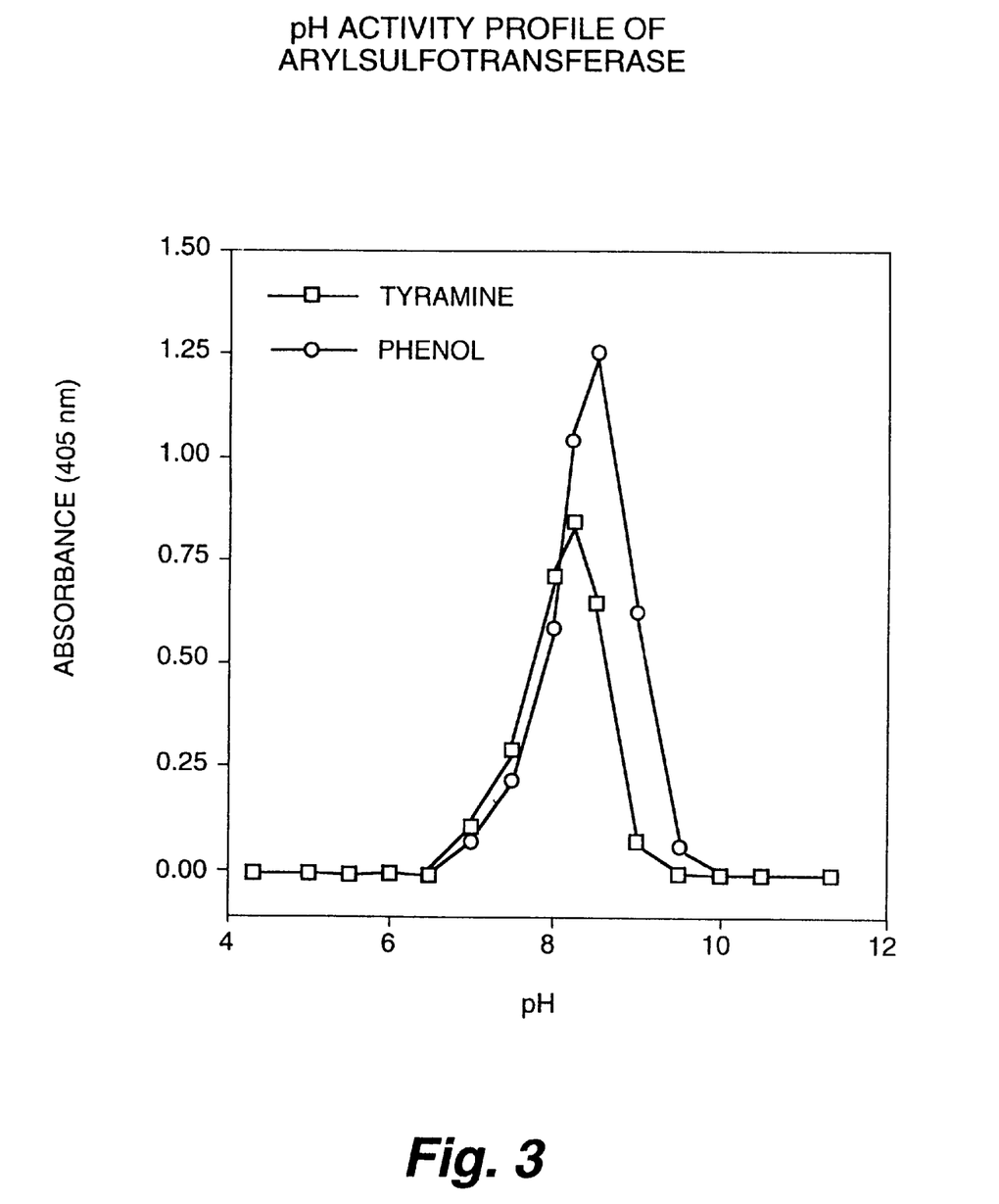
FIG. 3 shows the optimum pH for an arylsulfotransferase with two sulfate acceptors.

The enzyme was further analyzed by standard SDS-PAGE methods using a Pharmacia Phast minigel apparatus, which demonstrated that the enzyme has four subunits, each having a molecular weight of 80 kDaltons. The optimum pH for enzyme activity (FIG. 3) and the specific activity of the AST were determined in an assay using p-nitrophenylsulfate as a sulfate donor and tyramine (4-hydroxyphenethylamine) as a sulfate acceptor.

At each stage of purification, the AST activity was assayed by incubating the AST with 0.1 M Tris (pH 8.0), 5.0 mM p-nitrophenylsulfate (as aryl sulfate donor) and 2.5 mM tyramine (as sulfate acceptor). The reaction was incubated at 37° C. and terminated by addition of 1 N NaOH. The amount of p-nitrophenol formed during the reaction was determined by an absorbance reading at 405 nm. One unit of enzyme is equal to 1 mmol of p-nitrophenol formed per minute per milligram protein. Other aryl sulfate donors and phenolic acceptors were used at similar concentrations. Peptide acceptors were typically used in the 250–500 mM range. Formation of sulfated phenols and peptides was also quantitated via HPLC, using a 30% acetonitrile/70% water mobile phase. A UV detector was used to monitor peptides at 280 nm. Other wavelengths were used with various sulfated phenolic products and substrates as appropriate.

The above-described physical and biochemical properties of a *Clostridium innocuum* AST of the present invention are summarized in Table 3.

TABLE 3

PHYSICAL AND BIOCHEMICAL PROPERTIES OF ARYLSULFOTRANSFERASE

| | | |
|---|---|---|
| Molecular Weight | | 320,000 |
| Subunits | | 4 × 80,000 |
| Specific Activity | | 79.0 |
| Optimum pH | | 8.2 |
| $K_m$ (p-nitrophenylsulfate) | | 2.81 mM |
| $K_m$ (tyramine) | | 1.63 mM |
| Effectors | no effect: | EDTA |
| | | metals (Mn, Mg, Na, Fe, Ca, Cu, Ni, Co) |
| | | ATP |
| | inhibitory: | Zn |
| | stimulatory: | none identified |

Example 3

The following example shows that the AST of *Clostridium innocuum* 554 ATCC 55803 (Strain 554WT) can utilize a wide range of aryl sulfates as sulfate donors. Unlike the mammalian enzymes, the bacterial AST does not utilize 3'-phosphoadenosine-5'-phosphosulfate as a sulfate donor. The AST assay was performed as described in Example 2 using each of the sulfate donors listed in Table 4, with tyramine as the sulfate acceptor in each case. Table 4 shows the specificity of an arylsulfotransferase of the present invention for various sulfate donor substrates. Activity is shown as a percentage relative to the activity obtained with p-nitrophenylsulfate, which is designated as 100% activity.

TABLE 4

| Sulfate Donors | Activity (%) |
|---|---|
| p-nitrophenulsulfate | 100 |
| p-acetylphenylsulfate | 128 |
| 4-methylumbelliferyl sulfate | 46 |
| estrone sulfate | 22 |
| p-nitrocatechol sulfate | 196 |
| phenolphthalein sulfate | 12 |
| indoxyl sulfate | 35 |
| 3'-phosphoadenosine-5'-phosphosulfate | 0 |

Example 4

The following example shows that several phenolic compounds and tyrosylpeptides can serve as sulfate acceptors for an arylsulfotransferase of the present invention.

AST from *Clostridium innocuum* strain 554WT was used in a series of AST assays (as described in Example 2) to determine the ability of AST to catalyze the transfer of a sulfate group to a variety of acceptors. In each reaction, p-nitrophenylsulfate served as a sulfate donor. Table 5 shows the percent activity for several phenolic compounds as sulfate acceptors. Also shown are the percent yield obtained when tyrosylpeptides physalaemin (SEQ ID NO:1), kyotorphin (SEQ ID NO:2), dermorphin (SEQ ID NO:3), proctolin (SEQ ID NO:4), leu enkephalin (SEQ ID NO:5), cholecystokinin-8 (SEQ ID NO:6), angiotensin I (SEQ ID NO:7), caerulein (SEQ ID NO:8), arg8 vasopressin (SEQ ID NO:9), and hirudin (residues 54–65) (SEQ ID NO:10) were utilized as sulfate acceptors.

TABLE 5

| Sulfate Acceptors | | Activity (%) |
|---|---|---|
| Phenolic Compounds: | | |
| tyramine | | 100 |
| phenol | | 194 |
| tyrosine | | 13 |
| tyrosine methyl ester | | 59 |
| catechol | | 208 |
| catechin | | 150 |
| methyl p-hydroxybenzoate | | 65 |
| 4-methylumbelliferone | | 86 |
| Tyrosylpeptides: | | |
| Name | Amino Acid Sequence | Yield (%) |
| physalaemin (SEQ ID NO:1) | pGlu-Ala-Asp-Pro-Asn-Lys-Phe-Tyr-Gly-Leu-Metamide | 10.5 |
| kyotorphin (SEQ ID NO:2) | Tyr-Arg | 16.8 |
| dermorphin (SEQ ID NO:3) | Tyr-(D)-Ala-Phe-Gly-Tyr-Pro-Ser-amide | 67.0 |
| proctolin (SEQ ID NO:4) | Arg-Tyr-Leu-Pro-Thr | 19.8 |
| leu enkephalin (SEQ ID NO:5) | Tyr-Gly-Gly-Phe-Leu | 92.5 |
| cholecystokinin8 (SEQ ID NO:6) | Asp-Tyr-Met-Gly-Trp-Met-Asp-Phe-amide | 35.4 |
| angiotensin I (SEQ ID NO:7) | Asp-Arg-Val-Tyr-lle-His-Pro-Phe-Hid-Leu | 8.8 |
| caerulein | pGlu-Gln-Asp-Tyr-Thr-Gly-Trp- | 4.8 |

TABLE 5-continued

| | | |
|---|---|---|
| (SEQ ID NO:8) | Met-Asp-Phe-amide | |
| arg8 vasopressin (SEQ ID NO:9) | Cys-Tyr-Phe-Gln-Asn-Cys-Pro-Arg-Gly-amide | 35.8 |
| hirudin (54–65) (SEQ ID NO:10) | Gly-Asp-Phe-Glu-Glu-Ile-Pro-Glu-Glu-Tyr-Leu-Gln | 7.7 |

Example 5

The following example shows the apparent Km for a sulfate donor and a sulfate acceptor utilized by the arylsulfotransferase of the present invention.

Figure 4:
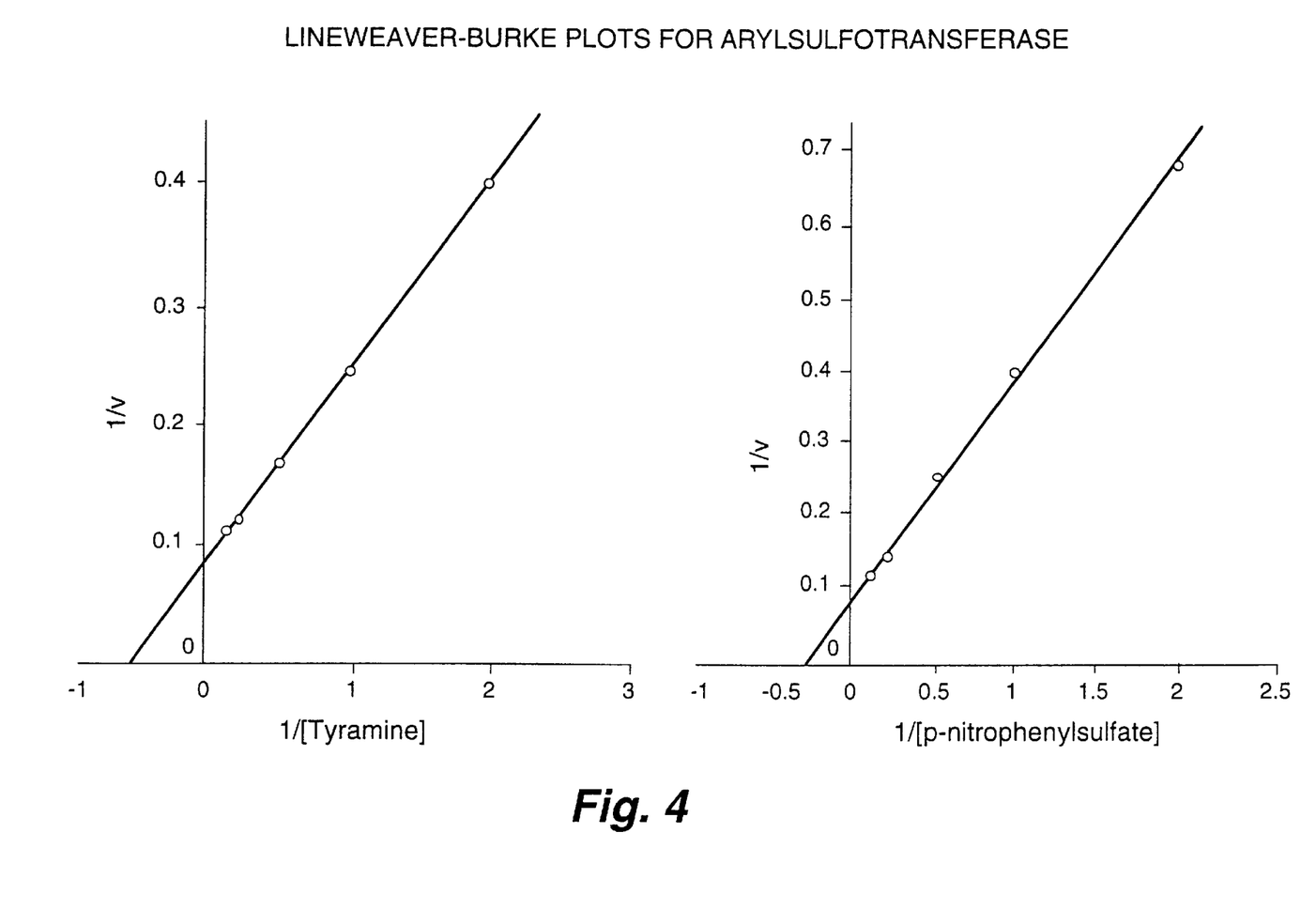
FIG. 4 shows the apparent Km for a sulfate acceptor and a sulfate donor in an arylsulfotransferase reaction using an arylsulfotransferase of the present invention.

In this AST assay, various concentrations of p-nitrophenylsulfate (as a sulfate donor) and of tyramine (as a sulfate acceptor) were plotted against the corresponding enzyme reaction rate in a double reciprocal plots (FIG. 4). AST activity was determined as described previously. The apparent Km for p-nitrophenylsulfate and for tyramine were calculated to be 2.81 mM and 1.63 mM, respectively.

Example 6

The following example shows the kinetics of *Clostridium innocuum* 554 ATCC 55803 (Strain 554WT) AST.

Figure 5:
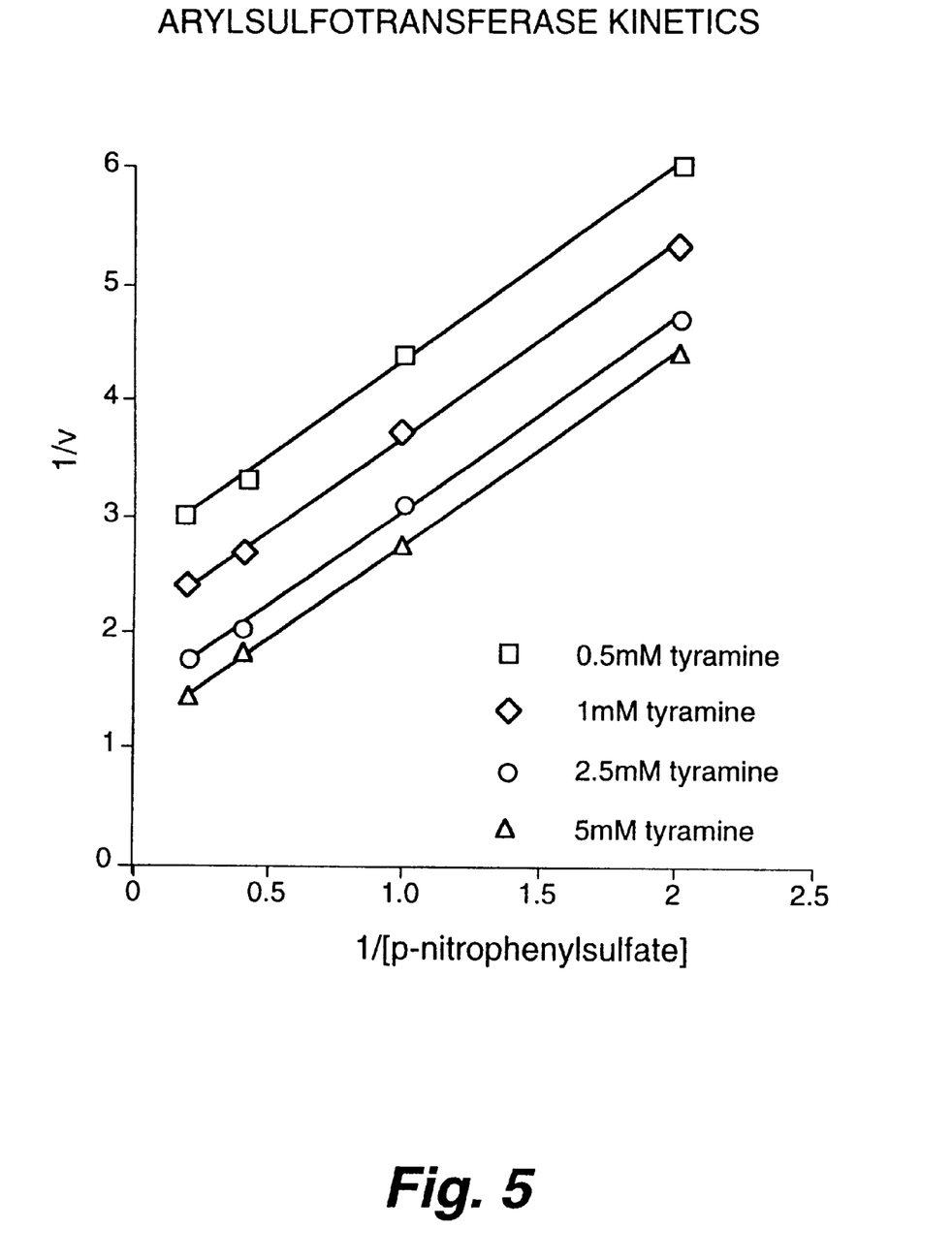
FIG. 5 shows the kinetics of an arylsulfotransferase of the present invention.

Reaction rates for AST were determined at several fixed concentrations of tyramine as a sulfate acceptor with variable concentrations of p-nitrophenylsulfate as the sulfate donor in an assay as described previously. FIG. 5 shows parallel lines as the tyramine concentration is increased. This suggests that the AST reaction proceeds according to a double-displacement (ping-pong) type mechanism.

What is claimed is:

1. An isolated Clostridium arysulfotransferase comprising the following characteristics:
   a. a total molecular weight of about 320 kD;
   b. 4 subunits having a molecular weight of about 80 kD each;
   c. an optimum pH for sulfation activity at about 8.2;
   d. a specific activity of greater than about 15.0 units per milligram of protein;
   e. an ability to maintain greater than about 40% activity for about 2 weeks when stored at 4° C. without being immobilized or otherwise protected; and
   f. an ability to use aryl sulfates selected from the group consisting of p-nitrophenylsulfate, p-acetylphenylsulfate, 4-methylumbelliferyl sulfate, estrone sulfate, p-nitrocatechol sulfate, phenolphthalein sulfate and indoxyl sulfate, as sulfate donors.

2. The arylsulfotransferase of claim 1, wherein said arylsulfotransferase is a naturally occurring *Clostridium innocuum* arylsulfotransferase.

3. The arylsulfotransferase of claim 1, wherein said arylsulfotransferase is isolated from *Clostridium innocuum* 554 ATCC 55803.

4. The arylsulfotransferase of claim 1, wherein said arylsulfotransferase catalyzes the transfer of a sulfate group to cholecystokinin-8 with a yield of greater than about 35% within about 6 hours.

5. The arylsulfotransferase of claim 1, wherein said arylsulfotransferase catalyzes the transfer of a sulfate group to cholecystokinin-8 with a yield of greater than about 45% within about 6 hours.

6. The arylsulfotransferase of claim 1, wherein said arylsulfotransferase catalyzes the transfer of a sulfate group to cholecystokinin-8 with a yield of greater than 55% within about 6 hours.

7. The arylsulfotransferase of claim 1, wherein said arylsulfotransferase sulfates a sulfate acceptor selected from the group consisting of a phenolic compound and a tyrosylpeptide.

8. The arylsulfotransferase of claim 7, wherein said sulfate acceptor is a phenolic compound selected from the group consisting of tyrosine, tyrosine methyl ester, tyramine, phenol, catechol, catechin, methyl p-hydroxybenzoate, 4-methylumbelliferone and methyl paraben.

9. The arylsulfotransferase of claim 7, wherein said sulfate acceptor is a tyrosylpeptide selected from the group consisting of cholecystokinin-8, kyotorphin, dermorphin, physalaemin, proctolin, angiotensin I, caerulein, arg8 vasopressin, hirudin(54–65) and leu enkephalin.

10. The arylsulfotransferase of claim 1, wherein said arylsulfotransferase maintains greater than about 60% activity at 4° C. for about 2 weeks without being immobilized or otherwise protected.

11. The arylsulfotransferase of claim 1, wherein said arylsulfotransferase maintains greater than about 80% activity at 4° C. for about 2 weeks without being immobilized or otherwise protected.

12. The arylsulfotransferase of claim 1, wherein said arylsulfotransferase has a donor substrate specificity for p-nitrophenylsulfate as a substrate donor of greater than about 60% activity, wherein 100% activity is measured using p-acetylphenylsulfate as a substrate donor, and wherein tyramine is a sulfate acceptor.

13. The arylsulfotransferase of claim 1, wherein said arylsulfotransferase has a donor substrate specificity for indoxyl sulfate as a substrate donor of greater than about 3% activity, wherein 100% activity is measured using p-acetylphenylsulfate as a substrate donor, and wherein tyramine is a sulfate acceptor.

14. The arylsulfotransferase of claim 1, wherein said arylsulfotransferase does not use 3'-phosphoadenosine-5'-phosphosulfate as a sulfate donor.

15. The arylsulfotransferase of claim 1, wherein said arylsulfotransferase has a donor substrate specificity for estrone sulfate as a substrate donor of greater than about 5% activity, wherein 100% activity is measured using p-acetylphenylsulfate as a substrate donor, and wherein tyramine is a sulfate acceptor.

* * * * *

UNITED STATES PATENT AND TRADEMARK OFFICE
CERTIFICATE OF CORRECTION

PATENT NO. : 6,225,100 B1
DATED : May 1, 2001
INVENTOR(S) : Maurina-Brunker et al.

It is certified that error appears in the above-identified patent and that said Letters Patent is hereby corrected as shown below:

Title page,
Item [73], Assignee, after DCV, Inc. add "d/b/a BioTechnical Resources"

Signed and Sealed this

Twentieth Day of November, 2001

Attest:

NICHOLAS P. GODICI
Attesting Officer
Acting Director of the United States Patent and Trademark Office